US009486283B2

(12) United States Patent
Greeley et al.

(10) Patent No.: US 9,486,283 B2
(45) Date of Patent: *Nov. 8, 2016

(54) FLUID-ASSISTED ELECTROSURGICAL DEVICE

(71) Applicant: Medtronic Advanced Energy LLC, Minneapolis, MN (US)

(72) Inventors: Roger D. Greeley, Portsmouth, NH (US); Donald Earles, Exeter, NH (US); David Flanagan, Somersworth, NH (US); Eliot Bloom, Hopkinton, NH (US); Brian Conley, South Berwick, ME (US); Jonathan Barry, Stratham, NH (US)

(73) Assignee: MEDTRONIC ADVANCED ENERGY LLC, Minneapolis, MN (US)

( * ) Notice: Subject to any disclaimer, the term of this patent is extended or adjusted under 35 U.S.C. 154(b) by 322 days.

This patent is subject to a terminal disclaimer.

(21) Appl. No.: 14/136,674

(22) Filed: Dec. 20, 2013

(65) Prior Publication Data

US 2014/0107647 A1    Apr. 17, 2014

Related U.S. Application Data

(62) Division of application No. 12/710,791, filed on Feb. 23, 2010, now Pat. No. 8,632,533.

(60) Provisional application No. 61/154,623, filed on Feb. 23, 2009.

(51) Int. Cl.
*A61B 18/14* (2006.01)
*A61B 18/18* (2006.01)
(Continued)

(52) U.S. Cl.
CPC ........... *A61B 18/18* (2013.01); *A61B 18/1402* (2013.01); *A61B 18/148* (2013.01); *A61B 2018/00029* (2013.01); *A61B 2018/0063* (2013.01); *A61B 2018/00345* (2013.01); *A61B 2018/00404* (2013.01); *A61B 2018/00434* (2013.01); *A61B 2018/00589* (2013.01); *A61B 2018/00601* (2013.01); *A61B 2018/00619* (2013.01); *A61B 2018/00642* (2013.01); *A61B 2018/00702* (2013.01); *A61B 2018/00791* (2013.01); *A61B 2018/00875* (2013.01);
(Continued)

(58) Field of Classification Search
CPC ............... A61B 2018/1417; A61B 2018/1405
USPC ......... 606/32, 33, 37, 39, 40, 41, 45, 48, 50
See application file for complete search history.

(56) References Cited

U.S. PATENT DOCUMENTS 2,888,928 A    6/1959 Seiger
3,682,130 A    8/1972 Jeffers
(Continued)

FOREIGN PATENT DOCUMENTS

DE    20 2007 013 012    12/2007
EP         1977706        8/2008

*Primary Examiner* — Jocelyn D Ram
(74) *Attorney, Agent, or Firm* — Jeffrey J. Hohenshell

(57) ABSTRACT

The disclosure provides a fluid-assisted electrosurgical device. The device comprises a first electrode, a second electrode and at least one fluid outlet. In one embodiment, the first electrode has a distal portion with an electrically conductive spherical surface, the second electrode has a distal portion with an electrically conductive spherical surface, and at least one of the first electrode and the second electrode have a blade portion.

19 Claims, 12 Drawing Sheets

(51) Int. Cl.
*A61B 18/00* (2006.01)
*A61B 18/12* (2006.01)

(52) U.S. Cl.
CPC .. *A61B2018/126* (2013.01); *A61B 2018/1253* (2013.01); *A61B 2018/1412* (2013.01); *A61B 2018/1415* (2013.01); *A61B 2018/1467* (2013.01); *A61B 2018/1472* (2013.01); *A61B 2218/002* (2013.01)

(56) References Cited

U.S. PATENT DOCUMENTS

| | | |
|---|---|---|
| 3,736,936 A | 6/1973 | Basiulis et al. |
| 3,750,650 A | 8/1973 | Ruttgers |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,060,088 A | 11/1977 | Morrison, Jr. et al. |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | van Gerven |
| 4,321,931 A | 3/1982 | Hon |
| 4,342,218 A | 8/1982 | Fox |
| 4,355,642 A | 10/1982 | Alfernes |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Scrochenko |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,936,281 A | 6/1990 | Stasz |
| 4,943,290 A | 7/1990 | Rexroth et al. |
| 4,946,460 A | 8/1990 | Merry et al. |
| 4,950,232 A | 8/1990 | Ruzicka et al. |
| 4,985,030 A | 1/1991 | Melzer et al. |
| 4,998,933 A | 3/1991 | Eggers et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Freidman et al. |
| 5,178,133 A | 1/1993 | Pena |
| 5,190,541 A | 3/1993 | Abele et al. |
| 5,195,959 A | 3/1993 | Smith |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,234,428 A | 8/1993 | Kaufman |
| 5,254,116 A | 10/1993 | Baust et al. |
| 5,254,117 A | 10/1993 | Rigby et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,417,709 A | 5/1995 | Slater |
| 5,423,807 A | 6/1995 | Mlilder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stern et al. |
| 5,443,470 A | 8/1995 | Stern et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |

(56) References Cited

U.S. PATENT DOCUMENTS

| | | |
|---|---|---|
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,562 A | 7/1996 | Giter |
| 5,542,945 A | 8/1996 | Fritzsch |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Sliwa, Jr. et al. |
| 5,562,702 A | 10/1996 | Huitema et al. |
| 5,562,720 A | 10/1996 | Stern et al. |
| 5,569,241 A | 10/1996 | Edwards |
| 5,569,243 A | 10/1996 | Kortenbach et al. |
| 5,571,088 A | 11/1996 | Lennox et al. |
| 5,571,215 A | 11/1996 | Sterman et al. |
| 5,573,424 A | 11/1996 | Poppe |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |
| 5,605,539 A | 2/1997 | Buelna et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,647,869 A | 7/1997 | Goble et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | LaFontaine |
| 5,678,550 A | 10/1997 | Bassen et al. |
| 5,680,860 A | 10/1997 | Imran |
| 5,681,278 A | 10/1997 | Igo et al. |
| 5,681,294 A | 10/1997 | Osborne et al. |
| 5,681,308 A | 10/1997 | Edwards et al. |
| 5,687,723 A | 11/1997 | Avitall |
| 5,687,737 A | 11/1997 | Branharn et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggars et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,735,290 A | 4/1998 | Sterman et al. |
| 5,743,903 A | 4/1998 | Stern et al. |
| 5,755,760 A | 5/1998 | Maguire et al. |
| 5,766,167 A | 6/1998 | Eggers et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,905 A | 8/1998 | Fleischman et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,764 A | 9/1998 | Eggers et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A * | 12/1998 | Tu .................. A61B 18/1492 606/41 |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,861,021 A | 1/1999 | Thome et al. |
| 5,871,523 A | 2/1999 | Fleischman et al. |
| 5,871,525 A | 2/1999 | Edwards et al. |
| 5,873,845 A | 2/1999 | Cline et al. |
| 5,873,855 A | 2/1999 | Eggers et al. |
| 5,876,399 A | 3/1999 | Chia et al. |
| 5,879,295 A | 3/1999 | Li et al. |
| 5,879,296 A | 3/1999 | Ockuly et al. |
| 5,879,348 A | 3/1999 | Owens et al. |
| 5,881,732 A | 3/1999 | Sung et al. |
| 5,882,346 A | 3/1999 | Pomeranz et al. |
| 5,885,278 A | 3/1999 | Fleischman |
| 5,891,142 A | 4/1999 | Eggers et al. |
| 5,893,848 A | 4/1999 | Negus et al. |
| 5,895,355 A | 4/1999 | Schaer |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,913,854 A | 6/1999 | Maguire et al. |
| 5,916,213 A | 6/1999 | Haissaguerre et al. |
| 5,916,214 A | 6/1999 | Cosio et al. |
| 5,919,191 A | 7/1999 | Lennox et al. |
| 5,921,924 A | 7/1999 | Avitall |
| 5,921,982 A | 7/1999 | Lesh et al. |
| 5,925,045 A | 7/1999 | Reimels et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,935,123 A | 8/1999 | Edwards et al. |
| 5,935,125 A * | 8/1999 | Zupkas .............. A61B 18/149 606/41 |
| 5,944,715 A | 8/1999 | Goble et al. |
| 5,944,718 A * | 8/1999 | Austin ............. A61B 18/1445 606/48 |
| 5,954,661 A | 9/1999 | Greenspon et al. |
| 5,957,919 A | 9/1999 | Laufer |
| 5,971,980 A | 10/1999 | Sherman |
| 5,971,983 A | 10/1999 | Lesh |
| 5,980,516 A | 11/1999 | Mulier et al. |
| 5,989,248 A | 11/1999 | Tu et al. |
| 5,993,412 A | 11/1999 | Deily et al. |
| 5,993,447 A | 11/1999 | Blewett et al. |
| 6,004,316 A | 12/1999 | Laufer |
| 6,004,319 A | 12/1999 | Goble et al. |
| 6,007,499 A | 12/1999 | Martin et al. |
| 6,010,500 A | 1/2000 | Sherman et al. |
| 6,012,457 A | 1/2000 | Lesh |
| 6,015,391 A | 1/2000 | Rishton et al. |
| 6,016,811 A | 1/2000 | Knopp et al. |
| 6,018,676 A | 1/2000 | Davis et al. |

(56) References Cited

U.S. PATENT DOCUMENTS

| | | | |
|---|---|---|---|
| 6,019,757 A | 2/2000 | Scheldrup |
| 6,024,733 A | 2/2000 | Eggers et al. |
| 6,030,381 A | 2/2000 | Jones et al. |
| 6,036,687 A | 3/2000 | Laufer et al. |
| 6,042,556 A | 3/2000 | Beach et al. |
| 6,048,333 A | 4/2000 | Lennox et al. |
| 6,056,744 A | 5/2000 | Edwards |
| 6,056,745 A | 5/2000 | Panescu et al. |
| 6,056,746 A | 5/2000 | Goble |
| 6,056,747 A | 5/2000 | Saadat et al. |
| 6,063,081 A | 5/2000 | Mulier |
| 6,066,139 A | 5/2000 | Ryan et al. |
| 6,068,653 A | 5/2000 | LaFontaine |
| 6,071,279 A | 6/2000 | Whayne et al. |
| 6,080,152 A * | 6/2000 | Nardella ............ A61B 18/1485 606/46 |
| 6,083,237 A | 7/2000 | Huitema et al. |
| 6,086,585 A | 7/2000 | Hovda et al. |
| 6,088,894 A | 7/2000 | Oakley |
| 6,096,037 A | 8/2000 | Mulier |
| 6,113,592 A | 9/2000 | Taylor |
| 6,113,596 A | 9/2000 | Hooven et al. |
| 6,117,101 A | 9/2000 | Diederich et al. |
| 6,120,496 A | 9/2000 | Whayne et al. |
| 6,141,576 A | 10/2000 | Littmann et al. |
| 6,142,993 A | 11/2000 | Whayne et al. |
| 6,142,994 A | 11/2000 | Swanson et al. |
| 6,149,620 A | 11/2000 | Baker et al. |
| 6,152,920 A | 11/2000 | Thompson et al. |
| 6,161,543 A | 12/2000 | Cox et al. |
| 6,165,174 A | 12/2000 | Jacobs et al. |
| 6,168,593 B1 * | 1/2001 | Sharkey ............... A61B 18/148 606/34 |
| 6,190,384 B1 | 2/2001 | Ouchi |
| 6,193,716 B1 | 2/2001 | Shannon, Jr. |
| 6,210,406 B1 | 4/2001 | Webster |
| 6,210,410 B1 | 4/2001 | Farin et al. |
| 6,210,411 B1 | 4/2001 | Hofmann et al. |
| 6,212,426 B1 | 4/2001 | Swanson |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,231,591 B1 | 5/2001 | Desai |
| 6,235,020 B1 | 5/2001 | Cheng et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,270,471 B1 | 8/2001 | Hechel et al. |
| 6,283,988 B1 | 9/2001 | Laufer et al. |
| 6,283,989 B1 | 9/2001 | Laufer et al. |
| 6,293,943 B1 | 9/2001 | Panescu et al. |
| 6,296,619 B1 | 10/2001 | Brisken et al. |
| 6,299,633 B1 | 10/2001 | Laufer |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,558,382 B2 | 5/2003 | Jahns |
| 6,558,385 B1 | 5/2003 | McClurken et al. |
| 5,697,536 C1 | 6/2003 | Eggers et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,673,072 B1 * | 1/2004 | Garito ............... A61B 18/1477 606/41 |
| 6,679,882 B1 | 1/2004 | Kornerup |
| 6,682,501 B1 * | 1/2004 | Nelson ............... A61B 5/0538 604/22 |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,726,684 B1 * | 4/2004 | Woloszko ............ A61B 18/148 606/32 |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |

(56) References Cited

U.S. PATENT DOCUMENTS

| | | | |
|---|---|---|---|
| 6,775,575 B2 | 8/2004 | Bommannan et al. |
| 6,776,780 B2 | 8/2004 | Mulier |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | McClurken et al. |
| 6,960,205 B2 | 11/2005 | Jahns |
| 6,962,589 B2 | 11/2005 | Mulier |
| 7,066,586 B2 | 6/2006 | Da Silva |
| 7,115,139 B2 | 10/2006 | McClurken et al. |
| 7,156,845 B2 | 1/2007 | Mulier et al. |
| 7,166,106 B2 | 1/2007 | Bartel et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,537,595 B2 | 5/2009 | McClurken |
| 7,604,635 B2 | 10/2009 | McClurken et al. |
| 7,645,277 B2 | 1/2010 | McClurken et al. |
| 7,651,494 B2 | 1/2010 | McClurken et al. |
| 7,736,361 B2 | 6/2010 | Palanker |
| 7,811,282 B2* | 10/2010 | McClurken ............ A61B 18/12 606/49 |
| 7,815,634 B2 | 10/2010 | McClurken et al. |
| 7,909,820 B2 | 3/2011 | Lipson |
| 7,942,872 B2 | 5/2011 | Ein-Gal |
| 7,976,544 B2 | 7/2011 | McClurken |
| 7,998,140 B2 | 8/2011 | McClurken |
| 8,012,154 B2 | 9/2011 | Livneh |
| 8,038,670 B2 | 10/2011 | McClurken |
| 8,048,070 B2 | 11/2011 | O'Brien |
| 8,080,009 B2 | 12/2011 | Lee et al. |
| 8,083,736 B2 | 12/2011 | McClurken et al. |
| 8,105,323 B2 | 1/2012 | Buysse et al. |
| 8,177,783 B2 | 5/2012 | Davison et al. |
| 8,323,276 B2 | 12/2012 | Palanker et al. |
| 8,632,533 B2 | 1/2014 | Greeley et al. |
| 8,801,705 B2* | 8/2014 | Sanders ............ A61B 18/1402 606/41 |
| 8,882,756 B2 | 11/2014 | Greeley et al. |
| 8,906,012 B2 | 12/2014 | Conley et al. |
| 8,920,417 B2 | 12/2014 | Conley et al. |
| 8,979,842 B2 | 3/2015 | McNall, III et al. |
| 2002/0049483 A1 | 4/2002 | Knowlton |
| 2002/0077626 A1* | 6/2002 | Ellman ............ A61B 18/1482 606/41 |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Shankey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0199226 A1 | 10/2004 | Shadduck |
| 2004/0215183 A1 | 10/2004 | Hoey |
| 2004/0220560 A1 | 11/2004 | Briscoe |
| 2004/0236322 A1 | 11/2004 | Mulier |
| 2004/0267258 A1* | 12/2004 | Zikorus ............ A61B 18/1492 606/41 |
| 2004/0267326 A1 | 12/2004 | Ocel |
| 2005/0010095 A1 | 1/2005 | Stewart et al. |
| 2005/0015085 A1 | 1/2005 | McClurken et al. |
| 2005/0033280 A1 | 2/2005 | Francischelli |
| 2005/0090815 A1 | 4/2005 | Francischelli |
| 2005/0090816 A1* | 4/2005 | McClurken ............ A61B 17/32 606/41 |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |
| 2006/0064085 A1 | 3/2006 | Schechter et al. |
| 2006/0149225 A1 | 7/2006 | McClurken |
| 2007/0049920 A1 | 3/2007 | McClurken et al. |
| 2007/0055226 A1* | 3/2007 | Garito ............ A61B 18/1402 606/41 |
| 2007/0093808 A1 | 4/2007 | Mulier et al. |
| 2007/0118114 A1 | 5/2007 | Miller et al. |
| 2007/0149964 A1* | 6/2007 | Kawabata ............ A61B 18/1492 606/41 |
| 2007/0208332 A1 | 9/2007 | Mulier et al. |
| 2008/0015563 A1 | 1/2008 | Hoey et al. |
| 2008/0071266 A1 | 3/2008 | Rioux |
| 2008/0071268 A1* | 3/2008 | Hafner ............ A61B 18/1442 606/48 |
| 2008/0071270 A1 | 3/2008 | Desinger et al. |
| 2008/0103494 A1 | 5/2008 | Rioux et al. |
| 2009/0222001 A1* | 9/2009 | Greeley ............ A61B 18/1402 606/33 |
| 2009/0264879 A1 | 10/2009 | McClurken et al. |
| 2009/0306655 A1 | 12/2009 | Stangeness |
| 2010/0100095 A1 | 4/2010 | McClurken et al. |
| 2010/0125272 A1* | 5/2010 | Scopton ......... A61B 17/320016 606/46 |
| 2010/0137856 A1* | 6/2010 | Burdio Pinilla ..... A61B 18/148 606/33 |
| 2011/0028965 A1 | 2/2011 | McClurken |
| 2011/0130757 A1* | 6/2011 | Horlle ............ A61B 18/1445 606/48 |
| 2011/0178515 A1 | 7/2011 | Bloom et al. |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0089141 A1* | 4/2012 | Lee .................. A61B 18/1477 606/41 |
| 2012/0101496 A1 | 4/2012 | McClurken et al. |
| 2012/0116397 A1 | 5/2012 | Rencher et al. |
| 2012/0150165 A1* | 6/2012 | Conley ............ A61B 18/1482 606/33 |
| 2012/0253343 A1 | 10/2012 | McClurken et al. |
| 2014/0188105 A1 | 7/2014 | Conley et al. |
| 2014/0276757 A1* | 9/2014 | Ellman ............ A61B 18/1402 606/33 |

\* cited by examiner

FLUID-ASSISTED ELECTROSURGICAL DEVICE

CROSS REFERENCE TO RELATED APPLICATIONS

This application is a divisional of U.S. application Ser. No. 12/710,791, filed Feb. 3, 2010, and entitled "Fluid-Assisted Electrosurgical Device"; which claims priority to U.S. provisional application Ser. No. 61/154,623, filed Feb. 23, 2009, which are incorporated by reference herein to the extent it is consistent.

FIELD

This disclosure relates generally to the field of medical devices, systems and methods for use upon a human body during surgery. More particularly, the disclosure relates to surgical devices, systems and methods that provide cutting of tissue as well as coagulation, hemostasis and sealing of tissue to inhibit blood and other fluid loss during surgery such as abdominal, orthopedic, spine and thoracic surgery as well as general surgery of the body.

BACKGROUND

Fluid-assisted electrosurgical devices have been developed which, when used in conjunction with an electrically conductive fluid such as saline, may be moved along a tissue surface, without cutting the tissue, to seal tissue to inhibit blood and other fluid loss during surgery. However, to cut tissue the surgeon must utilize a second device, which necessitates delays associated when switching between devices. What is still needed is an electrosurgical device which is capable of cutting of tissue as well as providing fluid-assisted sealing of tissue to inhibit blood and other fluid loss during surgery, as well as inhibit undesirable effects of tissue desiccation, tissue sticking to the electrode, tissue perforation, char formation and smoke generation.

SUMMARY

The disclosure, in one embodiment, may provide an electrosurgical device to treat tissue in a presence of a fluid from a fluid source and radio-frequency power from a radio-frequency power source, particularly providing a bipolar power output and a monopolar power output. The device may comprise a distal portion comprising a first electrode tip, a second electrode tip and at least one fluid outlet. The first and second electrode tips may be configured as bipolar electrodes, to receive the bipolar power output from the radio-frequency power source, and at least one of the electrode tips may be configured as a monopolar electrode, to receive the monopolar power output from the radio-frequency power source.

In certain embodiments, the at least one electrode tip configured as a monopolar electrode may provide an electrosurgical cutting edge, which may be configured to cut tissue by moving along a tissue surface in a presence of monopolar power output provided from the distal portion.

In certain embodiments, the at least one electrode tip configured as a monopolar electrode may comprise a blade portion. The blade portion may comprise opposing sides and an electrosurgical cutting edge. The electrosurgical cutting edge may extend from a proximal portion of the electrode tip to a distal portion of the electrode tip. The blade portion may narrow as the opposing sides approach the cutting edge.

In certain embodiments, at least one of the opposing sides may comprise a planar surface, concave surface or convex surface. Furthermore, the opposing sides may comprise opposing planer surfaces, concave surfaces or convex surfaces.

In certain embodiments, the first electrode tip and the second electrode tip may be configured to treat tissue by moving along a tissue surface in a presence of a bipolar power output and a fluid provided simultaneously from the distal portion.

In certain embodiments, the at least one fluid outlet may further comprise at least one fluid outlet in fluid communication with the first electrode tip, and at least one fluid outlet in fluid communication to the second electrode tip. The at least one fluid outlet in fluid communication with the first electrode tip may be proximal to a distal end of the first electrode tip, and the at least one fluid outlet in fluid communication with the second electrode tip may be proximal to a distal end of the second electrode tip. The at least one fluid outlet in fluid communication with the first electrode tip may be at least partially defined by the first electrode tip, and the at least one fluid outlet in fluid communication with the second electrode tip may be at least partially defined by the second electrode tip. The at least one fluid outlet in fluid communication with the first electrode tip may comprise a plurality of fluid outlets at least partially defined by the first electrode tip and the at least one fluid outlet in fluid communication with the second electrode tip may comprise a plurality of fluid outlets at least partially defined by the second electrode tip.

In certain embodiments, the first electrode tip may be laterally spaced from the second electrode tip. The first electrode tip may have a blunt distal end, and the second electrode tip may have a blunt distal end. The first electrode tip may also have a rounded distal end, and the second electrode tip may also have a rounded distal end. The first electrode tip and second electrode tip may be at a distal end of a shaft assembly.

In certain embodiments, an electrosurgical device to treat tissue in a presence of radio frequency energy and a fluid provided from the device may be provided, with the device comprising a distal portion comprising a first electrode tip, a second electrode tip and at least one fluid outlet. The first electrode tip may comprise a first electrode having a distal portion with an electrically conductive spherical surface, and the second electrode tip may comprise a second electrode having a distal portion with an electrically conductive spherical surface. At least one of the first electrode and the second electrode may have a blade portion.

In certain embodiments, the first electrode and the second electrode may be configured to be electrically coupled to a bipolar power output, and the at least one electrode having the blade portion may be configured to be electrically coupled to a monopolar power output. The blade portion may extend longitudinally along the electrode, from a proximal portion to the distal portion of the electrode. The blade portion may have a cutting edge, and more particularly have an electrosurgical cutting edge. The blade portion may have opposing sides, and narrow as the opposing sides approach the cutting edge. At least one of the opposing sides may comprise a planar surface, a concave surface or a convex surface.

In certain embodiments, the at least one fluid outlet may further comprise at least one fluid outlet in fluid communication with the first electrode and at least one fluid outlet in fluid communication with the second electrode. The at least one fluid outlet in fluid communication with the first electrode may be proximal to a distal end of the first electrode and at least partially defined by the first electrode, and the at least one fluid outlet in fluid communication with the second electrode may be proximal to a distal end of the second electrode and at least partially defined by the second electrode.

In certain embodiments, the first electrode may be laterally spaced from the second electrode. The first electrode may be carried by a first tubing segment at a distal end thereof, and the second electrode may be carried by a second tubing segment at a distal end thereof. The first electrode may be connected at a distal end of a first tubing segment, particularly mechanically joined to the first tubing segment, and the second electrode may be connected at a distal end of the second tubing segment, particularly mechanically joined to the second tubing segment. The first electrode also may be welded to the first tubing segment, and the second electrode may be welded to the second tubing segment.

In certain embodiments, the first tubing segment may be electrically conductive and in electrical contact with the first electrode, and the second tubing segment may be electrically conductive and in electrical contact with the second electrode.

In certain embodiments, an electrosurgical device having a distal portion comprising a first electrode tip, a second electrode tip and at least one fluid outlet may be provided, with the first electrode tip comprising a first electrode having a blade portion and the second electrode tip comprising a second electrode having a blade portion. The first and second electrodes may be configured to be electrically coupled to a bipolar energy source and at least one of the electrodes may be configured to be electrically coupled to a monopolar energy source. The first and second electrodes may be electrically coupled to the bipolar energy source by first and second bipolar electrical connectors in electrical communication with the first and second electrodes, respectively, and at least one of the electrodes may be electrically coupled to the monopolar energy source by a monopolar electrical connector in electrical communication with at least one of the electrodes.

DETAILED DESCRIPTION

Figure 1:
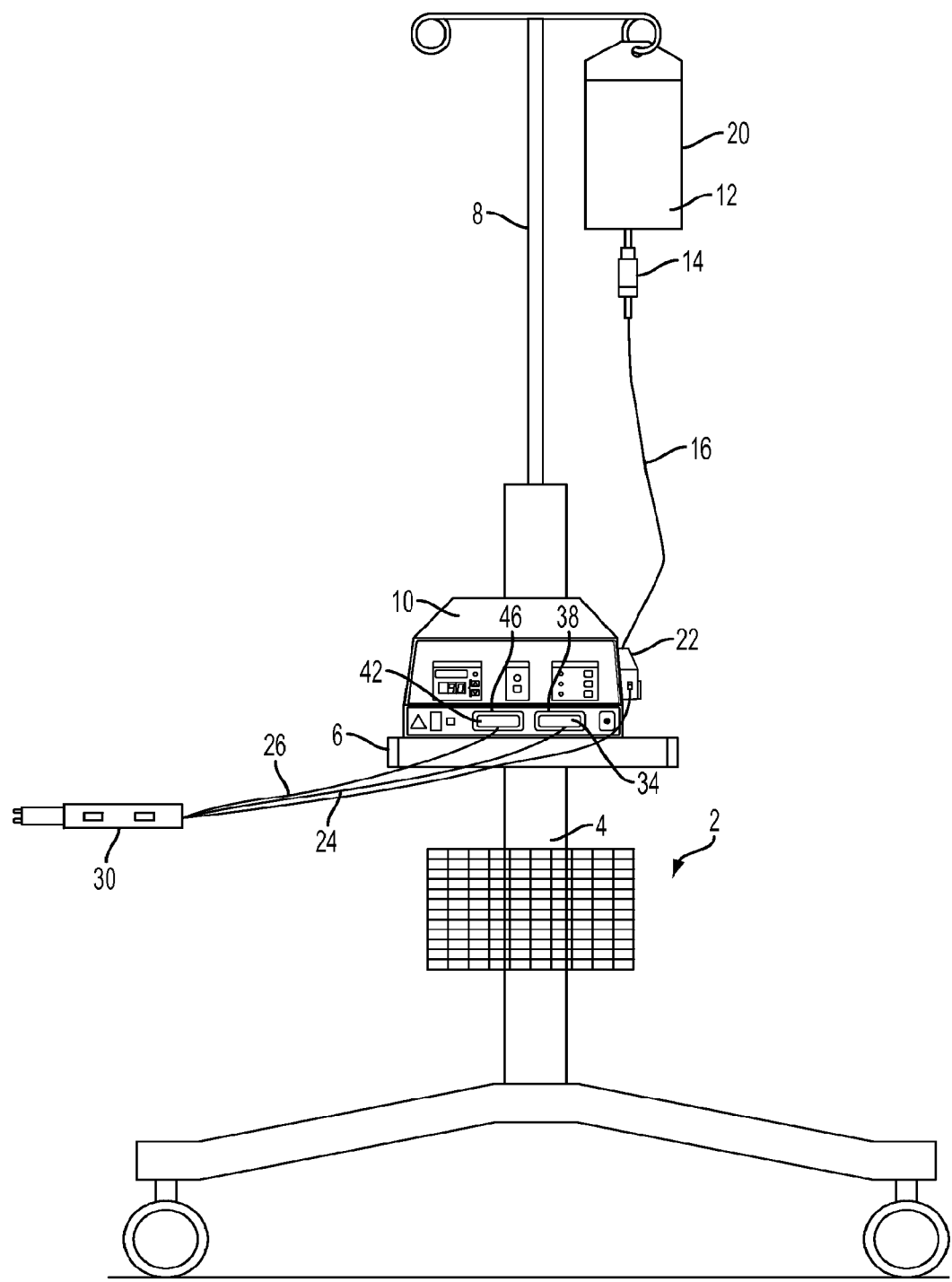
FIG. 1 is a front view of one embodiment of a system of the present disclosure having an electrosurgical unit in combination with a fluid source and handheld electrosurgical device.

Throughout the description, like reference numerals and letters indicate corresponding structure throughout the several views. Also, any particular feature(s) of a particular exemplary embodiment may be equally applied to any other exemplary embodiment(s) of this specification as suitable. In other words, features between the various exemplary embodiments described herein are interchangeable as suitable, and not exclusive. From the specification, it should be clear that any use of the terms "distal" and "proximal" are made in reference from the user of the device, and not the patient.

The disclosure provides devices, systems and methods for controlling tissue temperature at a tissue treatment site during an electrosurgical procedure, as well as shrinking, coagulating, cutting and sealing tissue against blood loss, for example, by shrinking lumens of blood vessels (e.g., arteries, veins).

The disclosure will now be discussed with reference to the figures, with FIG. 1 showing a front view of one embodiment of a system of the present disclosure having an exemplary electrosurgical unit 10 in combination with a fluid source 20 and a handheld electrosurgical device 30. FIG. 1 shows a movable cart 2 having a support member 4 comprising a hollow cylindrical post which carries a platform 6 comprising a pedestal table to provide a flat, stable surface for location of the electrosurgical unit 10.

As shown, cart 2 further comprises a fluid source carrying pole 8 having a height which may be adjusted by sliding the carrying pole 8 up and down within the support member 4 and thereafter secured in position with a set screw. On the top of the fluid source carrying pole 8 is a cross support provided with loops at the ends thereof to provide a hook for carrying fluid source 20.

As shown in FIG. 1, fluid source 20 comprises a bag of fluid from which the fluid 12 flows through a drip chamber 14 after the bag is penetrated with a spike located at the end of the drip chamber 14. Thereafter, fluid 12 flows through flexible delivery tubing 16 to handheld electrosurgical device 30. Preferably the fluid delivery tubing 16 is made from a polymer material.

As shown in FIG. 1, the fluid delivery tubing 16 passes through pump 22. As shown pump 22 comprises a peristaltic pump and, more specifically, a rotary peristaltic pump. With a rotary peristaltic pump, a portion of the delivery tubing 16 is loaded into the pump head by raising and lower the pump head in a known manner. Fluid 12 is then conveyed within the delivery tubing 16 by waves of contraction placed externally on the tubing 16 which are produced mechanically, typically by rotating pinch rollers which rotate on a drive shaft and intermittently compress the tubing 16 against an anvil support. Peristaltic pumps are generally preferred, as the electro-mechanical force mechanism, here rollers driven by electric motor, does not make contact the fluid 12, thus reducing the likelihood of inadvertent contamination.

In the present embodiment the fluid 12 comprises saline solution, and even more specifically, normal (physiologic) saline. Although the description herein may make reference to saline as the fluid 12, other electrically conductive fluids can be used in accordance with the disclosure.

While an electrically conductive fluid having an electrically conductivity similar to normal saline is preferred, as will become more apparent with further reading of this specification, fluid 12 may also comprise an electrically non-conductive fluid. The use of a non-conductive fluid, while not providing all the advantage of an electrically conductive fluid, still provides certain advantages over the use of a dry electrode including, for example, reduced occurrence of tissue sticking to the electrode of device 30 and cooling of the electrode and/or tissue. Therefore, it is also within the scope of the disclosure to include the use of a non-conducting fluid, such as, for example, deionized water.

Electrosurgical unit 10 is configured to provide both monopolar and bipolar power output. However, electrosurgical unit 10 includes a lock out feature which prevents both monopolar and bipolar output from being activated simultaneously. Alternatively, rather than use a single electrosurgical unit 10, device may be simultaneously connected to two separate electro surgical units. For example, device 30 may be connected to a first electrosurgical unit to provide monopolar power output and a second electrosurgical unit to provide bipolar power output.

During monopolar operation, a first electrode, often referred to as the active electrode, is provided with the monopolar electrosurgical device while a second electrode, often referred to as the indifferent or neutral electrode, is provided in the form of a ground pad dispersive electrode located on the patient (also known as a patient return electrode), typically on the back or other suitable anatomical location. An electrical circuit is formed between the active electrode and ground pad dispersive electrode with electrical current flowing from the active electrode through the patient to ground pad dispersive electrode in a manner known in the art. During bipolar operation, the ground pad electrode located on the patient is not required, and a second electrode providing an electrical pole is provided as part of the device. An alternating current electrical circuit is then created between the first and second electrical poles of the device. Consequently, alternating current no longer flows through the patient's body to the ground pad electrode, but rather through a localized portion of tissue between the poles of the bipolar device. Monopolar and bipolar power may be provided from electrosurgical unit 10 as known in the art, or from separate electrosurgical units.

Figure 6A:
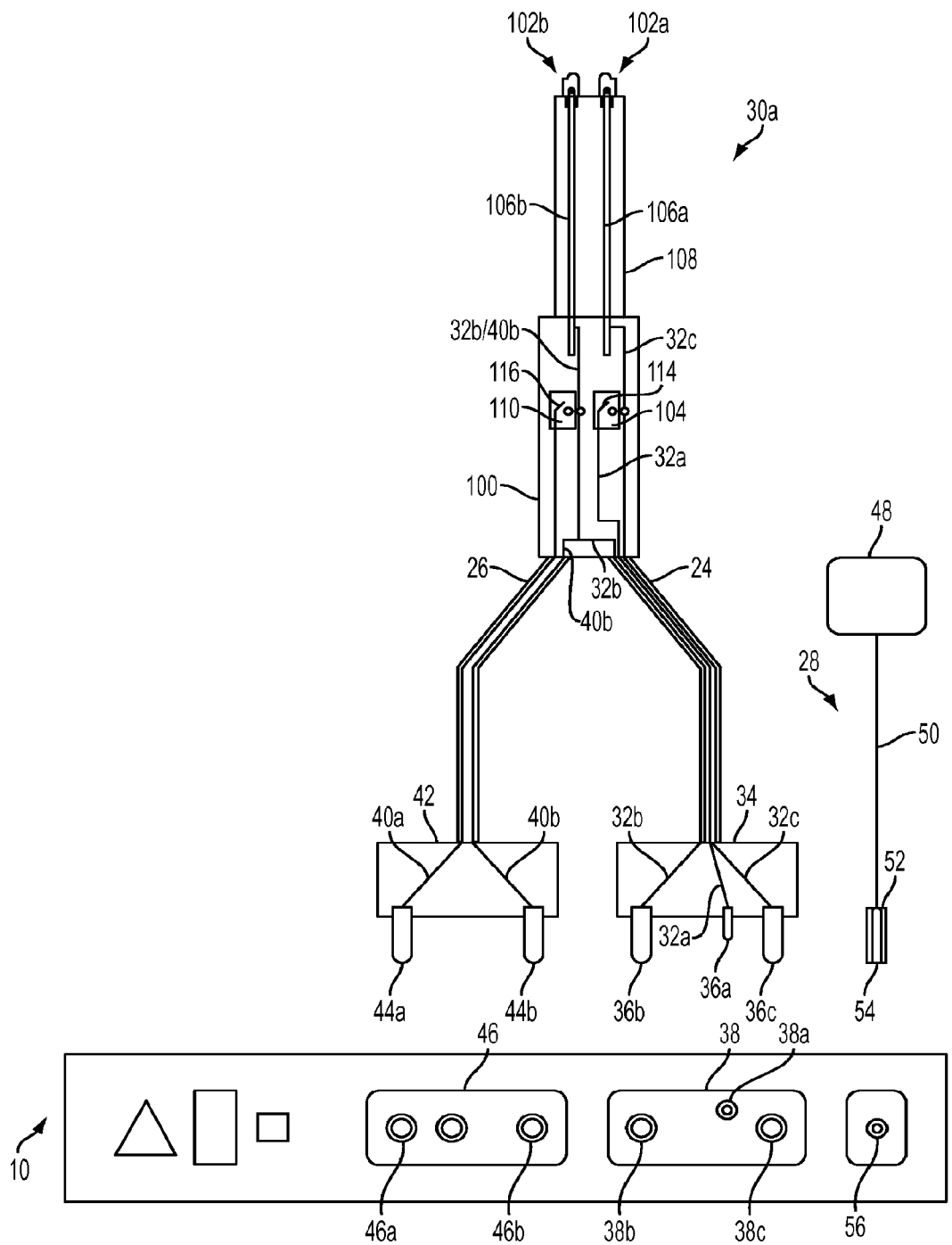
FIG. 6A is a plan view showing the various electrical connections and conductors of the device of FIG. 5 with the electro surgical unit of FIG. 1.

As shown in FIG. 1, electrosurgical device 30 is connected to electrosurgical unit 10 via electrical cables 24 and 26. Cable 24 has a plug 34 which connects to bipolar mode output receptacle 38 of electrosurgical unit 10. Cable 26 has a plug 42 which connects to the monopolar mode output receptacle 46 of electrosurgical unit 10. As shown in FIG. 6A, when electrosurgical 10 is used in monopolar mode, an additional cable 28 is utilized to connect a ground pad dispersive electrode 48 to the ground pad receptacle 56 of the electrosurgical unit 10.

Figure 2:
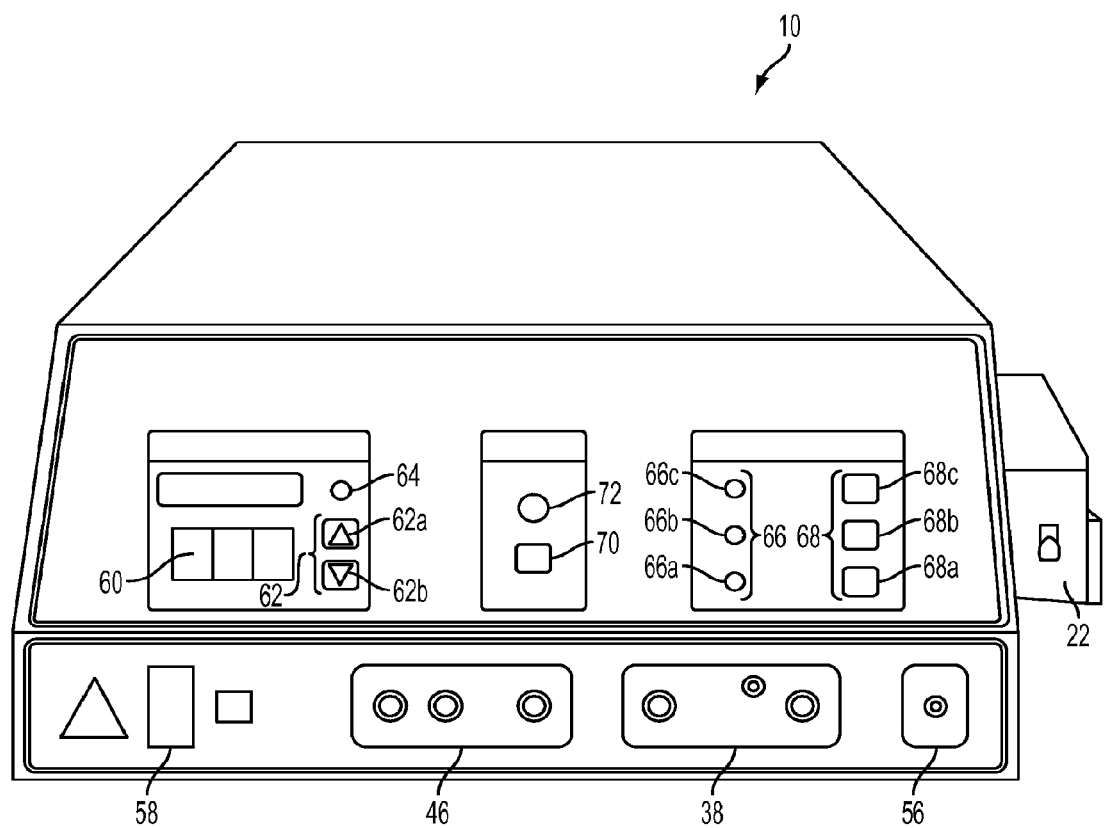
FIG. 2 a front perspective view of the electrosurgical unit of FIG. 1.

FIG. 2 shows the front panel of the exemplary electrosurgical unit 10. A power switch 58 may be used to turn the electrosurgical unit 10 on and off. After turning the electrosurgical unit 10 on, an RF power setting display 60 may be used to display the RF power setting numerically in watts. The power setting display 60 may further comprise a liquid crystal display (LCD).

Electrosurgical unit 10 may further comprise an RF power selector 62 comprising RF power setting switches 62a, 62b which may be used to select the RF power setting. Pushing the switch 62a may increase the RF power setting, while pushing the switch 62b may decrease the RF power setting. RF power output may be set in 5 watt increments in the range of 20 to 100 watts, and 10 watt increments in the range of 100 to 200 watts. Additionally, electrosurgical unit 10 may include an RF power activation display 64 comprising an indicator light which may illuminate when RF power is activated, either via a handswitch on device 30 or a footswitch. Switches 62a, 62b may comprise membrane switches. It should be understood that while only one RF power selector 62 is shown, electrosurgical unit 10 will have two such RF power selectors with one each for monopolar and bipolar power selection.

In addition to having a RF power setting display 60, electrosurgical unit 10 may further include a fluid flow rate setting display 66. Flow rate setting display 66 may comprise three indicator lights 66a, 66b and 66c with first light 66a corresponding to a fluid flow rate setting of low, second light 66b corresponding to a fluid flow rate setting of medium (intermediate) and third light 66c corresponding to a flow rate setting of high. One of these three indicator lights will illuminate when a fluid flow rate setting is selected.

Electrosurgical unit 10 may further include a fluid flow selector 68 comprising flow rate setting switches 68a, 68b and 68c used to select or switch the flow rate setting. Three push switches may be provided with first switch 68a corresponding to the fluid flow rate setting of low, second switch 68b corresponding to a fluid flow rate setting of medium (intermediate) and third switch 68c corresponding to a flow rate setting of high. Pushing one of these three switches may select the corresponding flow rate setting of either low, medium (intermediate) or high. The medium, or intermediate, flow rate setting may be automatically selected as the default setting if no setting is manually selected. Switches 68a, 68b and 68c may comprise membrane switches.

Before starting a surgical procedure, it may be desirable to prime device 30 with fluid 12. Priming may be desirable to inhibit RF power activation without the presence of fluid 12. A priming switch 70 may be used to initiate priming of device 30 with fluid 12. Pushing switch 70 once may initiate operation of pump 22 for a predetermined time period to prime device 30. After the time period is complete, the pump 22 may shut off automatically. When priming of device 30 is initiated, a priming display 72 comprising an indicator light may illuminate during the priming cycle.

Figure 3:
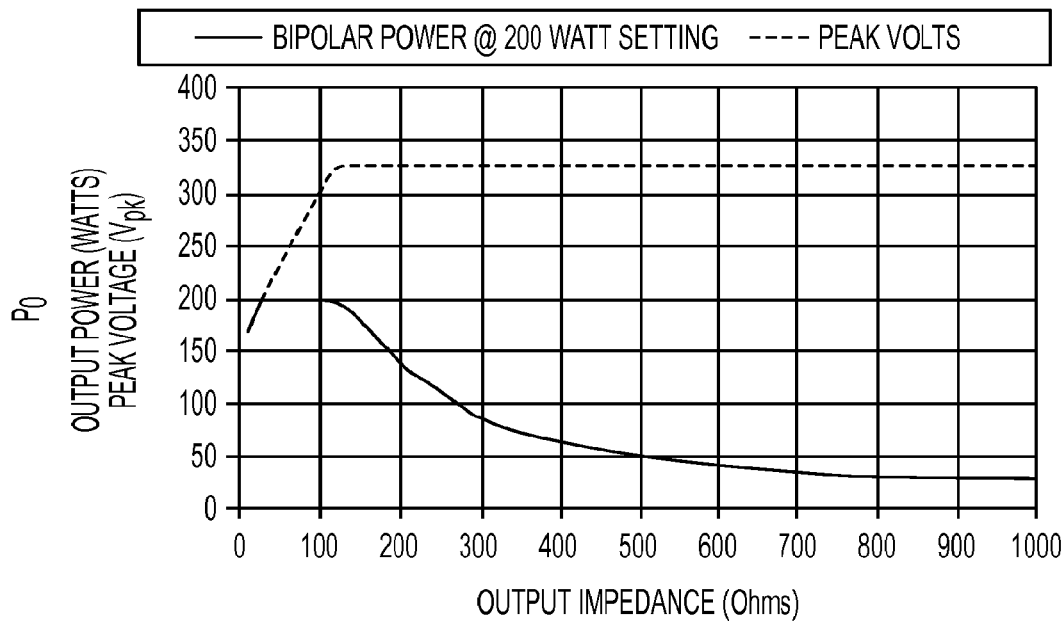
FIG. 3 is a graph of the bipolar RF power output versus impedance for the electrosurgical unit of FIG. 1.

An exemplary bipolar RF power output curve of electrosurgical unit 10 is shown in FIG. 3. Impedance Z, shown in units of ohms on the X-axis and output power $P_O$ is shown in units of watts on the Y-axis. In the illustrated embodiment, the bipolar electrosurgical power (RF) is set to 200 watts. As shown in the figure, for an RF power setting $P_S$ of 200 watts, the output power $P_O$ will remain constant with the set RF power PS as long as the impedance Z stays between the low impedance cut-off of 30 ohms and the high impedance cut-off of 120 ohms. Below an impedance Z of 30 ohms, the output power $P_O$ will decrease as shown by the low impedance ramp. Above an impedance Z of 120 ohms, the output power $P_O$ will also decrease as shown by the high impedance ramp. With respect to monopolar power output, an exemplary monopolar RF power output curve would include that of the Valleylab Force FX, hereby incorporated by reference.

Figure 4:
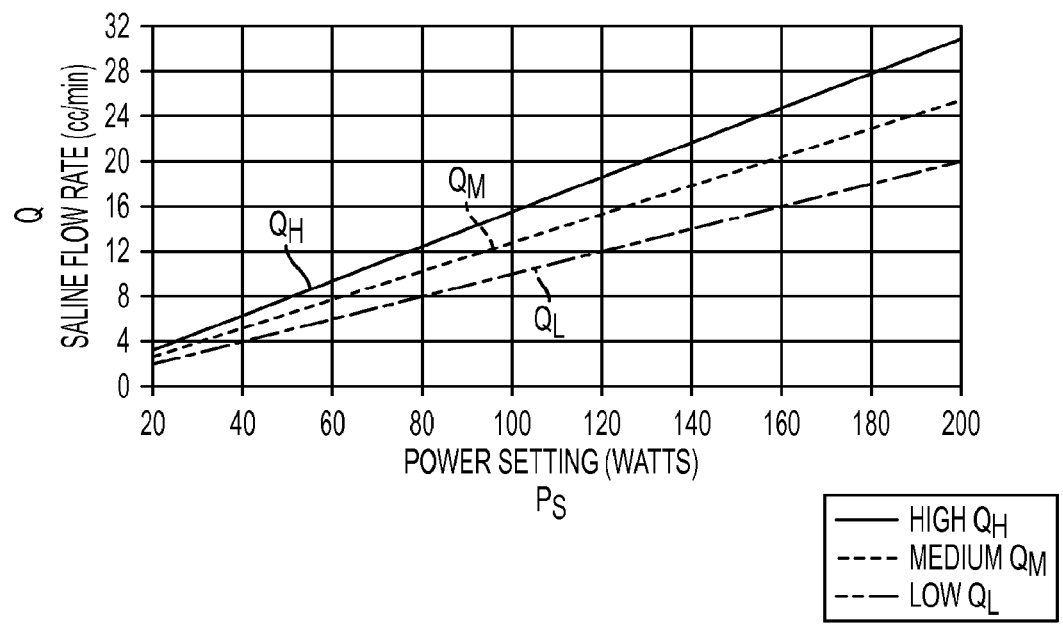
FIG. 4 is graph showing a relationship of fluid flow rate Q in units of cubic centimetres per minute (cc/min) on the Y-axis, and the RF power setting $P_S$ in units of watts on the X-axis.

Electrosurgical unit 10 may be configured such that the speed of pump 22, and therefore the throughput of fluid 12 expelled by the pump 22, is predetermined based on two input variables, the RF power setting and the fluid flow rate setting. In FIG. 4 there is shown an exemplary functional relationship of fluid flow rate Q in units of cubic centimetres per minute (cc/min) on the Y-axis, and the RF power setting $P_S$ in units of watts on the X-axis. The relationship may be engineered to inhibit undesirable effects such as tissue desiccation, electrode sticking, smoke production and char formation, while at the same time not providing a fluid flow rate Q at a corresponding RF power setting $P_S$ which is so great as to provide too much electrical dispersion and cooling at the electrode/tissue interface. While not being bound to a particular theory, a more detailed discussion on how the fluid flow rate interacts with the radio frequency power, modes of heat transfer away from the tissue, fractional boiling of the fluid and various control strategies may be found in U.S. Publication No. 2001/0032002, published Oct. 18, 2001, assigned to the assignee of the present disclosure and hereby incorporated by reference in its entirety to the extent it is consistent.

As shown in FIG. 4, electrosurgical unit 10 has been configured to increase the fluid flow rate Q linearly with an increasing RF power setting $P_S$ for each of three fluid flow rate settings of low, medium and high corresponding to $Q_L$, $Q_M$ and $Q_H$, respectively. Conversely, electrosurgical unit 10 has been configured to decrease the fluid flow rate Q linearly with a decrease RF power setting $P_S$ for each of three fluid flow rate settings of low, medium and high corresponding to $Q_L$, $Q_M$ and $Q_H$, respectively.

An electrosurgical unit similar to exemplary electrosurgical unit 10 and having detailed schematic drawings, albeit without monopolar output, may be found in U.S. Publication No. 2006/0149225, published Jul. 6, 2006, assigned to the assignee of the present disclosure and hereby incorporated by reference in its entirety to the extent it is consistent.

While electrosurgical unit 10 as shown above includes an attached pump 22, in other embodiments pump 22 may not be integrated with electrosurgical unit 10, but rather be separate from electrosurgical unit 10.

In still other embodiments, pump 22 may be eliminated and there may be no preset functional relationship of fluid flow rate Q versus RF power setting $P_S$ stored in the electrosurgical unit 10. In such an instance, rather than the fluid flow rate Q being automatically controlled by the electrosurgical unit 10 based on the RF power setting $P_S$, the fluid flow rate Q may be manually controlled, such as by the user of device 10 or another member of the surgical team, with a roller (pinch) clamp or other clamp provided with device 10 and configured to act upon and compress the tubing 16 and control flow in a manner known in the art. Exemplary fluid flow control mechanisms may be found in U.S. Publication No. 2005/0090816, published Apr. 28, 2005, assigned to the assignee of the present disclosure and hereby incorporated by reference in its entirety to the extent it is consistent. An example of an electrosurgical unit which does not include a pump, but may be used in conjunction with a manually operated fluid flow control mechanism on device 10, includes an electrosurgical unit such as the Valleylab Force FX.

Figure 5:
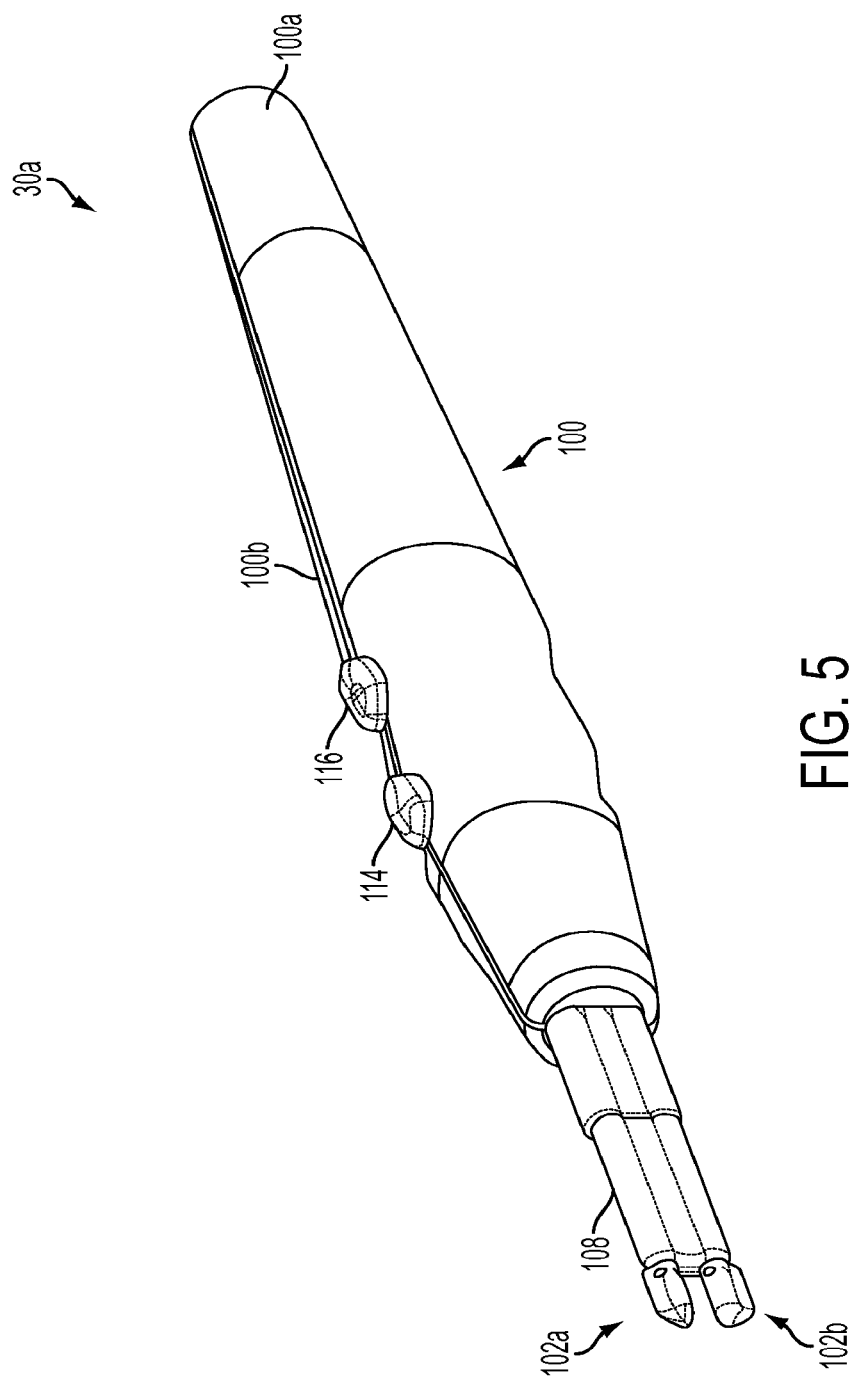
FIG. 5 is a perspective view of an electrosurgical device according to the present disclosure.

An exemplary bipolar and/or monopolar electrosurgical device of the present disclosure which may be used in conjunction with electrosurgical unit 10 of the present disclosure is shown at reference character 30a in FIG. 5.

While various electrosurgical devices of the present disclosure are described herein with reference to use with electrosurgical unit 10, it should be understood that the description of the combination is for purposes of illustrating the system of the disclosure. Consequently, it should be understood that while the electrosurgical devices disclosed herein may be disclosed for use with electrosurgical unit 10, it may be plausible to use other electrosurgical devices with electrosurgical unit 10, or it may be plausible to use the electrosurgical devices disclosed herein with another electrosurgical unit.

As shown in FIG. 5, exemplary device 30a comprises an elongated handle 100 comprising mating handle portions 100a, 100b. Handle 100 is slender, along with the rest of device 30a, to enable a user of device 30a to hold and manipulate device 30a between the thumb and index finger like a pen-type device. Handle 100 may comprise a sterilizable, rigid, non-conductive material, such as a polymer (e.g., polycarbonate).

As best shown in FIG. 6A, device 30a also comprises cables 24 and 26 which are connectable to electrosurgical unit 10 to provide device 30a with bipolar and monopolar power output, respectively, from electrosurgical unit 10. As shown, cable 24 of device 30a comprises three insulated wire conductors 32a, 32b, 32c connectable to bipolar power output receptacles 38a, 38b, 38c of electrosurgical unit 10 via three banana (male) plug connectors 36a, 36b, 36c. The banana plug connectors 36a, 36b, 36c are each assembled with insulated wire conductors 32a, 32b, 32c within the housing of plug 34 in a known manner. On device 30a, insulated wire conductor 32a is connected to a bipolar hand switch assembly 104, and insulated wire conductors 32b and 32c are connected to semi-circular barrel crimp terminals which snap connect to a proximal portion of shafts 106a, 106b of shaft assembly 108.

Cable 26 of device 30a comprises two insulated wire conductors 40a, 40b connectable to monopolar power output receptacles 46a, 46b of electrosurgical unit 10 via two banana (male) plug connectors 44a, 44b. The banana plug connectors 44a, 44b are each assembled with insulated wire conductors 40a, 40b within the housing of plug 42 in a known manner. On device 30a, insulated wire conductor 40a is connected to a monopolar hand switch assembly 110, and insulated wire conductor 40b is connected to a semi-circular barrel crimp terminal which snap connects to a proximal portion of shaft 106b of shaft assembly 108. When device 30a is used in monopolar mode, an additional cable 28 is utilized to connect a ground pad dispersive electrode 48 which is attached to the patient to the electrosurgical unit 10 comprising wire conductor 50 and plug 52 at the end thereof having plug connector 54 which connects to the ground pad receptacle 56. As shown wire conductors 32b and 40b merge inside handle 100 and share the same attachment location to shaft 106b.

Hand switch assemblies 104 and 110 may comprise push buttons 114 and 116, respectively, (best shown in FIG. 5) which overlie domed switches on a platform comprising a printed circuit board, with the construction and wiring of the hand switch assemblies 104 and 110 known in the art. Upon depression of push buttons 114 or 116, a domed switch beneath the push button forms a closed circuit which is sensed by electrosurgical unit 10, which then provides bipolar or monopolar power, respectively. Exemplary hand switches may be found in U.S. Publication No. 2006/0149225, published Jul. 6, 2006, and U.S. Publication No. 2005/0090816, published Apr. 28, 2005, which are assigned to the assignee of the present disclosure and are hereby incorporated by reference in there entirety to the extent they are consistent.

Figure 6B:
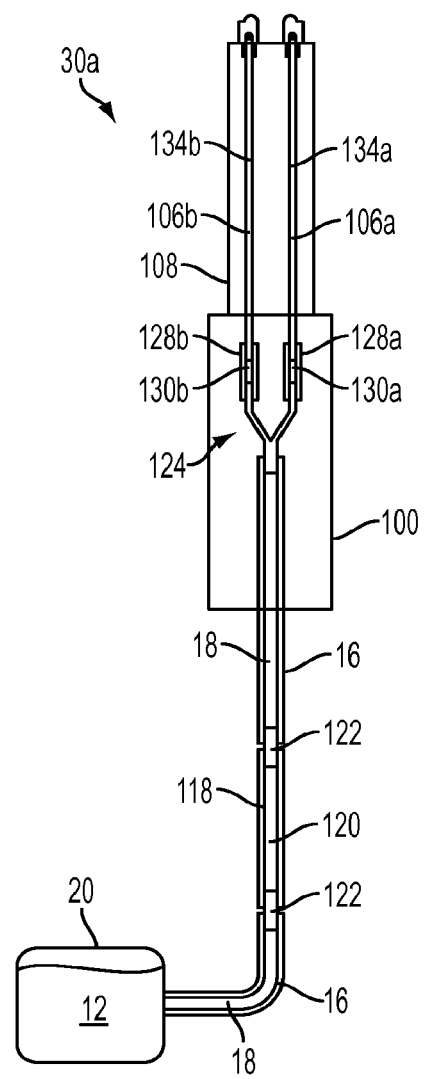
FIG. 6B is a plan view showing the various fluid connections and passages of the device of FIG. 5 with the electrosurgical unit and fluid source of FIG. 1.

As shown FIG. 6B, during use of device 30a, fluid 12 from fluid source 20 is communicated through a tubular fluid passage which provided by various structures. In the present embodiment, fluid 12 from the fluid source 20 is first communicated through lumen 18 of delivery tubing 16. Fluid 12 may also flow through lumen 120 of a special pump tubing segment 118 designed to operate specifically with the peristaltic pump 22, which may be spliced in between portions of delivery tubing 16 and connected thereto using barbed fluid line connectors 122 at each end thereof.

Within handle 100 of device 30a, fluid delivery tubing 16 is connected to the inlet branch of a Y-splitter 124, which thereafter provides two outlet branches which are connected to the proximal ends of polymer delivery tubing segments 128a, 128b. The distal ends of delivery tubing segments 128a, 128b are thereafter connected to the proximal ends of shafts 106a, 106b. To connect delivery tubing 128a, 128b to shafts 106a, 106b, the lumens 130a, 130b are preferably interference fit over the outside diameter of shafts 106a, 106b to provide an interference fit seal there between. Fluid 12 then may flow through the lumens 134a, 134b of shafts 106a, 106b.

Once the semi-circular barrel crimp terminals and delivery tubing segments 128a, 128b are connected to shafts 106a, 106b, a polymer shrink wrap tubing may then be heat shrink wrapped around the connections to better electrically insulate the shafts 106a, 106b and better secure the connections.

Figure 7:
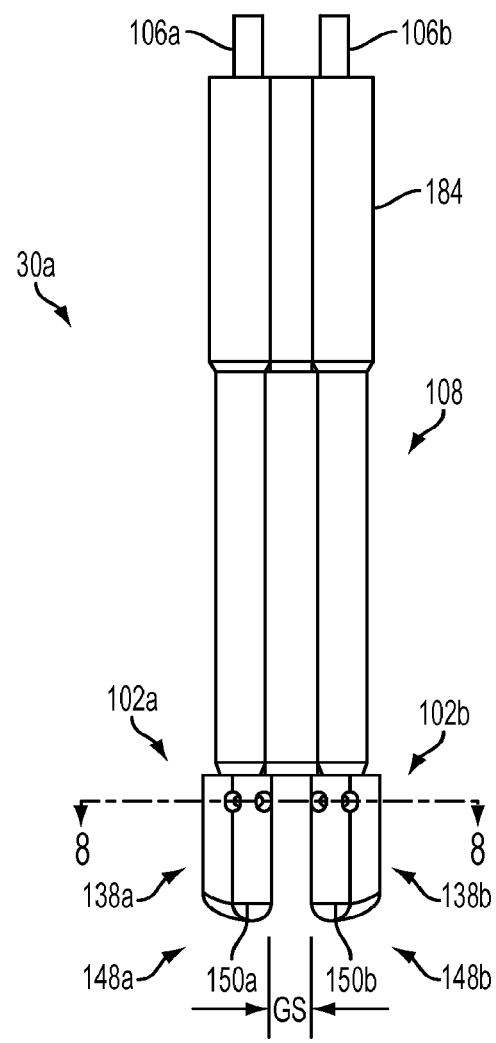
FIG. 7 is a close-up view of the shaft assembly of the device of FIG. 5.

As best shown in FIG. 7, shaft assembly 108 of the present embodiment comprises two parallel, self-supporting, electrically conductive hollow shafts 106a, 106b, which comprise metal tubing segments, such as stainless steel tubing segments. Carried by and connected to the distal ends of shafts 106a, 106b are two laterally and spatially separated (by empty space) contact elements in the form of electrode tips comprising electrodes 102a, 102b which may be configured as mirror images in size and shape, and have a blunt distal end with a surface devoid of edges (to provide a uniform current density) to treat tissue. In the present embodiment electrodes 102a, 102b comprise an electrically conductive material, particularly metal, such as stainless steel. Other suitable materials may include titanium, gold, silver and platinum.

In certain embodiments, the tubing segments of one or both shafts 106a, 106b may be made of electrically non-conducting material except for the portion at the distal end that comes in physical and electrical contact with electrodes 102a, 102b. In these embodiments, an insulated wire conductor would extend and be joined to the electrically conducting portion of shaft 106a, 106b. In still other embodiments, shafts 106a, 106b may completely comprise electrically non-conducting material, in which case an insulated wire conductor would extend and be joined directly to electrodes 102a, 102b.

As shown in FIG. 7, each electrode 102a, 102b comprises an elongated portion 138a, 138b. With respect to length, in the present embodiment elongated portion 138a, 138b has a length in the range between and including about 2 mm to 6 mm, and more specifically have a length of about 3 mm to 5 mm. With respect to spacing, in the present embodiment the spatial gap separation GS between electrodes 102a, 102b in the range between and including about 0.1 mm to about 4 mm, and more specifically about 1 mm to 2.5 mm, and more specifically about 1.5 mm to 2.3 mm.

Figure 8:
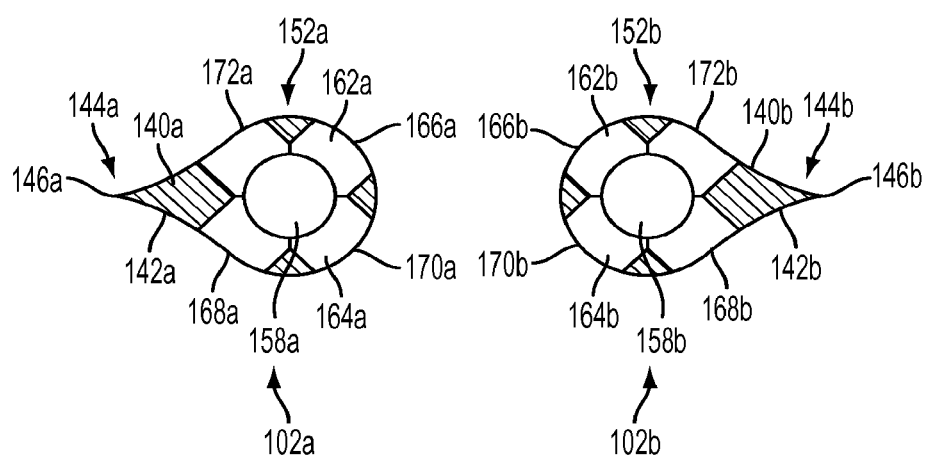
FIG. 8 is a close-up cross-sectional view of the electrodes of the device of FIG. 5 taken along line 8-8 of FIG. 7.

As best shown in FIG. 8, opposing sides 140a/142a of elongated portion 138a, and opposing sides 140b/142b of elongated portion 138b converge laterally to provide a wedge shaped blade portion 144a, 144b which terminates in a lateral cutting edge 146a, 146b which extends longitudinally along a length of each electrode 102a, 102b. As shown in FIG. 8, lateral cutting edge 146a, 146b extends from a proximal to distal portion of each electrode 102a, 102b, as well as transitions onto the distal end of each electrode 102a, 102b and forms a portion of the distal end of each electrode 102a, 102b.

Lateral cutting edge 146a, 146b is preferably configured to cut tissue electrosurgically in the presence of monopolar radio frequency energy from electrosurgical unit 10 as to provide an electrosurgical cutting edge, but without any fluid 12 being provided from fluid source 20. However, in other embodiments, lateral cutting edge 146a, 146b may be configured to cut tissue with fluid 12 being provided simultaneously from device 30a, or be configured to cut tissue mechanically without electrosurgical energy. Furthermore, while two cutting edges 146a, 146b are shown, only one of the edges 146a or 146b needs to be configured to cut tissue electrosurgically or mechanically. In such instance, the blade portion of the electrode may be eliminated and the elongated portion may be completely cylindrical.

Figure 9:
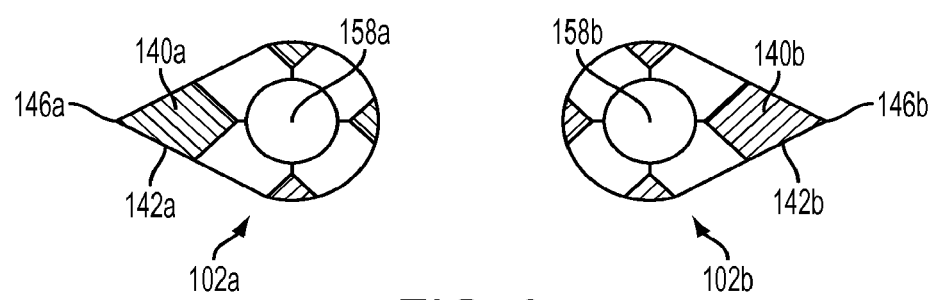
FIG. 9 is a close-up view of the shape of the electrodes of another embodiment of the device of FIG. 5 taken along line 8-8 of FIG. 7.
Figure 10:
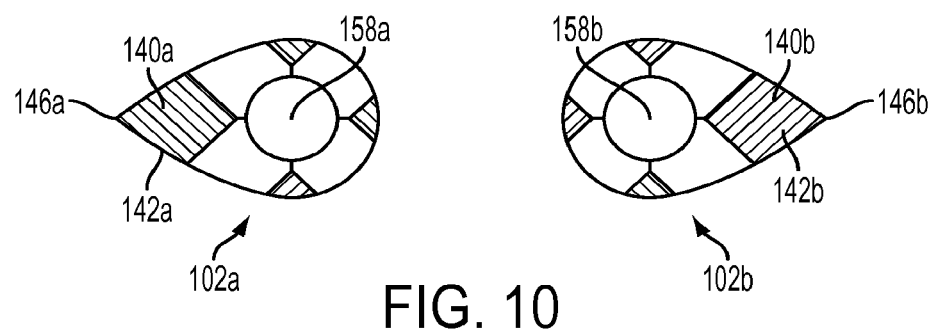
FIG. 10 is a close-up view of the shape of the electrodes of another embodiment of the device of FIG. 5 taken along line 8-8 of FIG. 7.

As shown in FIG. 8, blade portion 144a, 144b narrows as the opposing sides 140a/142a and 140b/142b approach cutting edge 146a, 146b. More particularly, as shown in FIG. 8, the sides 140a/142a and 140b/142b of blade portion 144a, 144b are concave. However, in other embodiments, sides 140a/142a and 140b/142b may be planar or convex as shown in FIGS. 9 and 10, respectively. Also, in other embodiments, only one of sides 140a/142a and 140b/142b may be concave, planar or convex.

Returning to FIG. 7, electrodes 102a, 102b and elongated portions 138a, 138b terminate in distal end portion 148a, 148b. The distal end portion 148a, 148b of electrodes 102a, 102b are configured to slide across a tissue surface in the presence of bipolar radio frequency energy from electrosurgical unit 10 and fluid 12 from the fluid source 20. As shown, the distal end portion 148a, 148b of each electrode 102a, 102b has a blunt, rounded shape which provides a smooth contour surface which is devoid of points or edges. More specifically, as shown, distal end portion 148a, 148b of each electrode 102a, 102b has a spherical surface provided by spherical portion 150a, 150b. In the present embodiment, spherical portion 150a, 150b has a radius in the range between and including about 0.5 mm to 1.5 mm, and more specifically about 0.75 mm to 1.15 mm.

Figure 11:
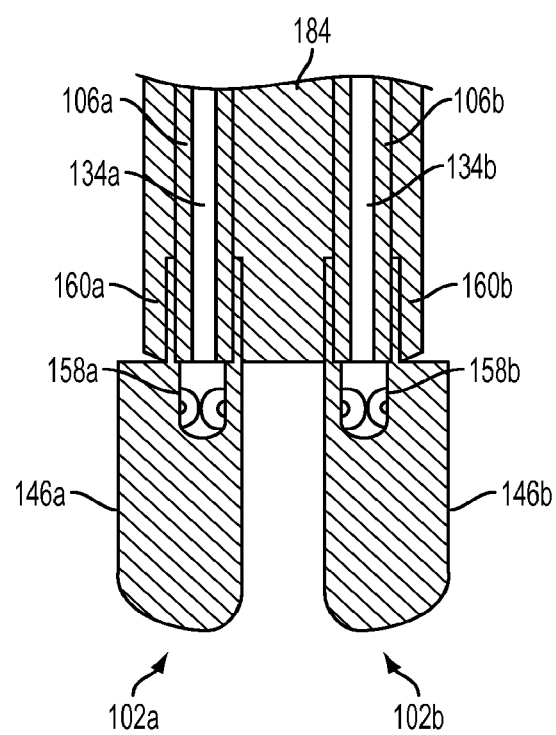
FIG. 11 is a close-up cross-sectional view of a distal end portion of the device of FIG. 5 taken perpendicular to line 8-8 of FIG. 7.

As best shown in FIGS. 8 and 11, within a cylindrical portion 152a, 152b of each electrode 102a, 102b proximal to distal end portion 148a, 148b, each electrode 102a, 102b includes a longitudinally oriented linear blind bore 158a, 158b and counter bore 160a, 160b. As shown in FIG. 11, the outside diameter of a distal end portion of each shaft 106a, 106b is configured to extend into counter bore 160a, 160b of electrodes 102a, 102b and fit with the diameter of counter bore 160a, 160b, with the distal end of each shaft 106a, 106b in contact with the bottom of the counter bore. The electrodes 102a, 102b and shafts 106a, 106b may then be welded together to connect the two components. In alternative embodiments, the outside diameter of shafts 106a, 106b may be configured to fit with the diameter of counter bore 160a, 160b and mechanically join in the form of a press (interference) fit to provide a secure connection. In other alternative embodiments, electrodes 102a, 102b may be assembled to shafts 106a, 106b by threaded engagement. In still other embodiments, electrodes 102a, 102b may be detachably assembled to shafts 106a, 106b such that they may be removed from the shafts 106a, 106b, preferably manually by human hand.

In addition to blind bore 158a, 158b and counterbore 160a, 160b, as shown in FIG. 8, electrodes 102a, 102b also include a through bores 162a/164a and 162b/164b which perpendicularly intersects bore 158a, 158b and perpendicularly intersect one another to provide outlets 166a/168a/170a/172a and 166b/168b/170b/172b (for fluid 12) which are in fluid communication with electrodes 102a, 102b. Thus, after fluid 12 flows through the lumens 134a, 134b of shafts 106a, 106b, fluid 12 then flows through into the tubular passage provided by blind bore 158a, 158b and then into the tubular passage provided by through bores 162a/164a and 162b/164b where it thereafter exits device 30a from fluid outlets 166a/168a/170a/172a and 166b/168b/170b/172b, which are all proximal to distal end portion 148a, 148b of electrodes 102a, 102b. As shown in FIG. 8, fluid outlets 166a/170a and 166b/170b are at least partially defined by the cylindrical portion 152a, 152b of electrodes 102a, 102b, while fluid outlets 168a/172a and 168b/172b are at least partially defined by sides of 140a/142a and 140b/142b of blade portion 144a, 144b and adjacent cutting edge 146a, 146b. More particularly, as shown in FIG. 8, fluid outlets 166a/170a and 166b/170b are fully defined by the cylindrical portion 152a, 152b of electrodes 102a, 102b, while fluid outlets 168a/172a and 168b/172b are fully defined by sides of 140a/142a and 140b/142b of blade portion 144a, 144b and adjacent cutting edge 146a, 146b. In certain embodiments, each electrode 102a, 102b may have only one fluid outlet in fluid communication therewith, such as outlets 168a, 168b. In still other embodiments, only a single one fluid outlet may be present.

The relationship between the material for electrodes 102a, 102b and their surfaces, and fluid 12 throughout the various embodiments should be such that the fluid 12 wets the surface of the electrodes 102a, 102b. Contact angle, $\theta$, is a quantitative measure of the wetting of a solid by a liquid. It is defined geometrically as the angle formed by a liquid at the three phase boundary where a liquid, gas and solid intersect. In terms of the thermodynamics of the materials involved, contact angle $\theta$ involves the interfacial free energies between the three phases given by the equation $$\gamma_{LV} \cos \theta = \gamma_{SV} - \gamma_{SL}$$

where $\gamma_{LV}$, $\gamma_{SV}$ and $\gamma_{SL}$ refer to the interfacial energies of the liquid/vapor, solid/vapor and solid/liquid interfaces, respectively. If the contact angle $\theta$ is less than 90 degrees the liquid is said to wet the solid. If the contact angle is greater than 90 degrees the liquid is non-wetting. A zero contact angle $\theta$ represents complete wetting. Thus, preferably the contact angle is less than 90 degrees.

As best shown in FIGS. 7 and 11, a portion of the lengths of shafts 106a, 106b are surrounded by and encapsulated in a common outer member 184, which may comprises a flexible polymer. Outer member 184 electrically insulates the exposed length of shafts 106a, 106b.

Outer member 184 may be formed by injection molding. During the injection molding process, a sub-assembly comprising electrodes 102a, 102b and shafts 106a, 106b is placed in the injection mold prior to the introduction of polymer. Thereafter, the mold is closed and a thermoplastic polymer may be injected into the unoccupied portions of the mold cavity to overmold and mold-in place portions of the sub-assembly as shown in FIG. 7. During the injection molding process, retainer clips (not shown) may provide the benefit of retaining shafts 106a, 106b in position relative to each other to better ensure that the shafts 106a, 106b are centrally located within the polymer molding.

To be hand shapeable by surgeons and other users of device 30a, so that the device 30a may be used in a greater multitude of angles and locations, at least a portion of shafts 106a, 106b of device 30a may be malleable to provide a malleable shaft assembly 108. Also, in this manner, a distal portion of shafts 106a, 106b may be bendable at an angle relative to the longitudinal axis of the proximal portion of shafts 106a, 106b during manufacturing of device 30a so they may be provided to users of device 30a at various angles. For example, angle may range from about 5 degrees to 90 degrees, and more preferably, about 15 degrees to 45 degrees, and even more preferably about 30 degrees. As used herein, malleable means able to be shaped, particularly by bending (without a mechanical mechanism, such as a hinge or joint). It should be understood that shaft assembly 108 is to independently maintain the shape associated with the selected bent shape, and does not require additional components (e.g., pull wires, etc.) to maintain the selected bent shape. Furthermore, shaft assembly 108 is to maintain the selected shape such that when device 30a is used to treat tissue, and will not overtly deflect from the selected shape. Furthermore, shaft assembly 108 is constructed such that a user can readily re-shape the shafts back to a straight state and/or other desired bent configurations.

Outer member 184, in addition to electrically insulating shafts 106a, 106b from one another, has been found to be particularly useful in facilitating the hand shaping of shafts 106a, 106b of shaft assembly 108 simultaneously and with a similar contour without cracking. In this manner, surgeons and other users of device 30a need not bend the shafts 106a, 106b individually, and the relative spacing and position of the electrodes 102a, 102b may be maintained constant.

To provide malleability, shafts 106a, 106b preferably have an outer wall diameter of about 0.063 inches and an inner wall diameter of about 0.032 inches. Shafts 106a, 106b also preferably are made from 304 stainless steel with a temper from about ½ to ¾ hard, 130,000 to 150,000 psi. (pounds per square inch) tensile strength) and an elongation at break of about 40%. Shafts 106a, 106b with the foregoing properties provide sufficient stiffness as not to be too pliable during normal use of device 30a, while at the same time inhibiting the shafts 106a, 106b from kinking or breaking when shaped for application. When the wall thickness is too thin, shafts 106a, 106b may kink, and when the wall thickness is too thick, the shafts 106a, 106b may be too stiff. Furthermore, a shaft 106a, 106b with a larger diameter may also kink more than a shaft of smaller diameter. Shafts 106a, 106b may also be malleable for a portion of the length or full length depending on application. For example, the shafts 106a, 106b can be made with variable stiffness along the length and be malleable only for a distal portion thereof. Preferably this is performed by controlled annealing of the shafts 106a, 106b only in the area where malleability is desired.

Figure 12:
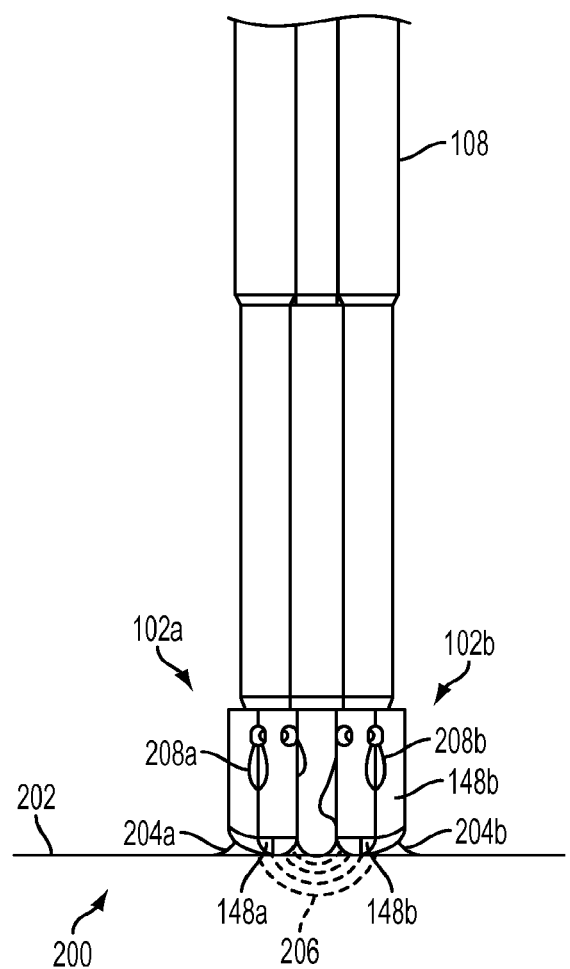
FIG. 12 is a close-up view of a distal end portion of the device of FIG. 5 with an exemplary fluid coupling to a tissue surface of tissue.

As shown in FIG. 12, one way in which device 30a may be used is with the longitudinal axis of electrodes 102a, 102b vertically orientated, and the distal end portion 148a, 148b of electrodes 102a, 102b laterally spaced adjacent tissue surface 202 of tissue 200. When device 30a is used in this manner, electrodes 102a, 102b are connected to electrosurgical unit 10 and receive bipolar radio frequency energy which forms an alternating current electrical field in tissue 200 located between electrodes 102a, 102b. In the presence of alternating current, the electrodes 102a, 102b alternate polarity between positive and negative charges with current flow from the positive to negative charge. Without being bound to a particular theory, heating of the tissue is performed by electrical resistance heating.

Fluid 12, in addition to providing an electrical coupling between the device 30a and tissue 200, lubricates surface 202 of tissue 200 and facilitates the movement of electrodes 102a, 102b across surface 202 of tissue 200. During movement of electrodes 102a, 102b, electrodes 102a, 102b typically slide across the surface 202 of tissue 200. Typically the user of device 30a slides electrodes 102a, 102b across surface 202 of tissue 200 back and forth with a painting motion while using fluid 12 as, among other things, a lubricating coating. Preferably the thickness of the fluid 12 between the distal end portions 148a, 148b of electrodes 102a, 102b and surface 202 of tissue 200 at the outer edge of couplings 204a, 204b is in the range between and including about 0.05 mm to 1.5 mm. Also, in certain embodiments, the distal end portion 148a, 148b of electrodes 102a, 102b may contact surface 202 of tissue 200 without any fluid 12 in between.

As shown in FIG. 12, fluid 12 expelled from fluid outlets may form into droplets 208a, 208b which flow distally on electrodes 102a, 102b. As shown in FIG. 12, droplets 208a, 208b may form at varying times from fluid 12 expelled from any one of the fluid outlets. Also, fluid 12 may be expelled in varying quantity from each of the fluid outlets, depending on, for example, device orientation, pressure, flow rate and varying fluid outlet sizes. With use of device 30a, the size of droplets 208a, 208b may also vary due to changes in the surface finish of the electrodes 102a, 102b, for example, as a result of being contaminated by blood and tissue.

Figure 13:
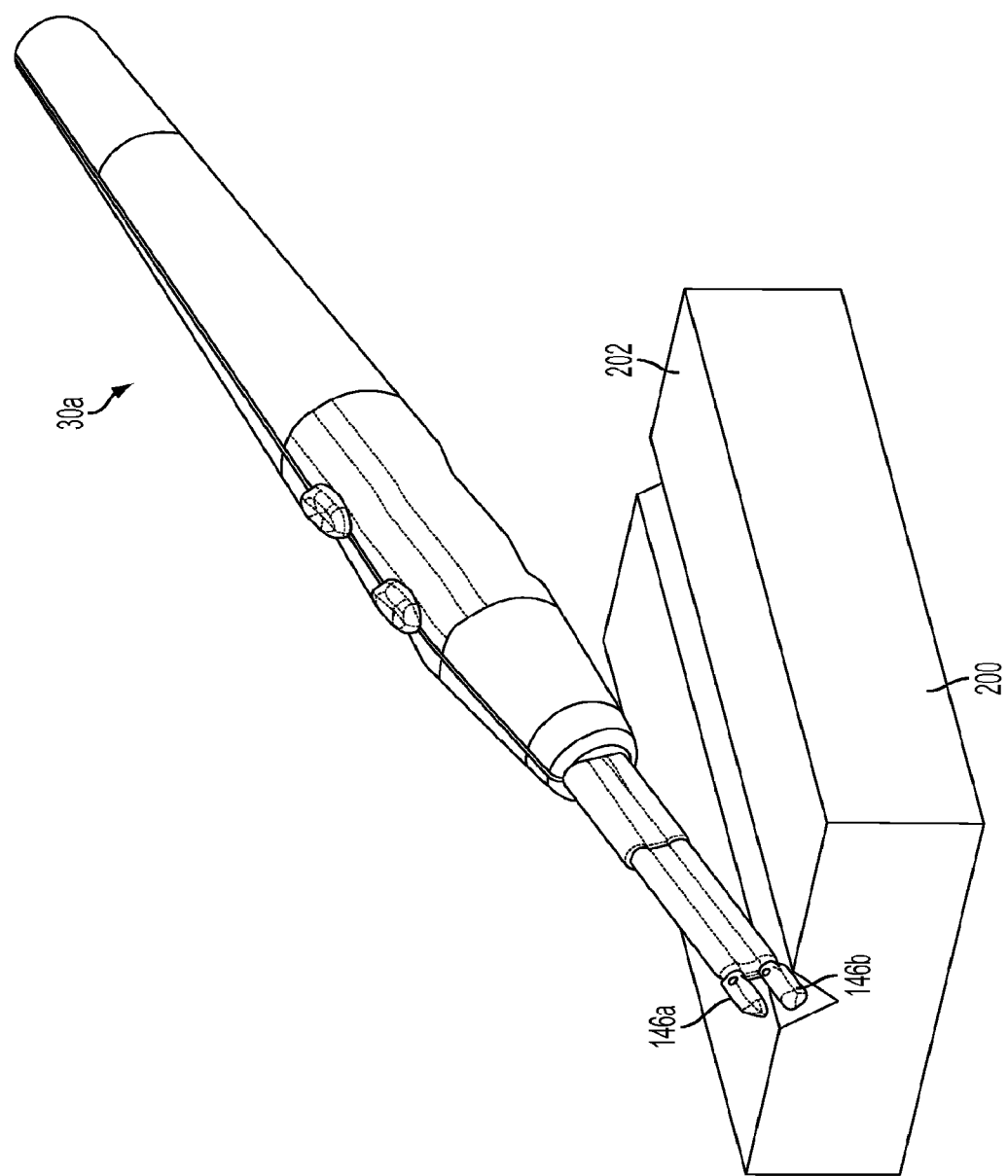
FIG. 13 is a perspective view of the device of FIG. 5 cutting tissue.

As shown in FIG. 12, fluid couplings 204a, 204b comprise discrete, localized webs and more specifically comprise triangular shaped webs or bead portions providing a film of fluid 12 between surface 202 of tissue 200 and electrodes 102a, 102b. When the user of electrosurgical device 30a places electrodes 102a, 102b at a tissue treatment site and moves electrodes 102a, 102b across the surface 202 of the tissue 200, fluid 12 is expelled from fluid outlets 166a/168a/170a/172a and 166b/168b/170b/172b around the surfaces of electrodes 102a, 102b and onto the surface 202 of the tissue 200 via couplings 204a, 204b. At the same time, RF electrical energy, shown by electrical field lines 206, is provided to tissue 200 at tissue surface 202 and below tissue surface 202 into tissue 200 through fluid couplings 204a, 204b. As shown in FIG. 13, device 30a may be used to cut tissue by applying either cutting edge 146a or 146b to tissue 200, depending which electrode 102a, 102b is utilized, and repeatedly moving the electrode 102a or 102b along a desired incision or resection line in the tissue to form the depicted crevice.

Device 30a may be used to perform a solid organ resection such as a liver resection. Edge 146a or 146b may be first used to score the outer capsule of the liver along the planned line of resection. Thereafter, the distal end portions 148a, 148b of electrodes 102a, 102b may be moved back and forth along the line, with radio frequency power and the flow of fluid on, resulting in coagulation of the liver parenchyma beneath the scored capsule. As the tissue is coagulated under and around the electrode surfaces, the electrodes 102a, 102b may be used to separate and blunt dissect the coagulated parenchyma and enter the resulting crevice. As the distal end portions 148a, 148b of electrodes 102a, 102b treat the parenchyma, the treated parenchyma looses integrity and becomes easier to separate, either alone or in conjunction with separation force applied by electrodes 102a, 102b from the user of the device.

Blunt dissection of the coagulated parenchyma is performed by continuous abrading or splitting apart of the parenchyma with substantially the same back and forth motion as coagulation and with the device 30a being held substantially in the same orientation as for coagulation of the liver parenchyma. However, with blunt dissection, the surgeon typically applies more force to the tissue. In various embodiments, once the liver parenchyma is coagulated, blunt dissection may be performed with or without the radio frequency power (i.e., on or off) and/or with or without the presence of fluid from device 30a. Additionally or alternatively, the tissue on opposing sides of the line of resection may be placed into tension perpendicular to the line of resection to facilitate resection. Furthermore, resection may also be accomplished by sharp dissection with edge 146a or 146b of electrodes 102a, 102b. Thus, with device 30a, a surgeon may perform a resection procedure in a number of different ways.

As the parenchyma is resected, blood vessels within the parenchyma may be uncovered which extend across or transverse the line of resection. Device 30a may be used to shrink and seal these vessels by heating and shrinking the collagen contained in the walls of the vessels thus decreasing the diameter of the lumen of these vessels. For vessels with a diameter too large to completely occlude the lumen, the vessels may be tied with suture on each side of the line of resection and thereafter severed therebetween. If such vessels are not first uncovered by removing the surrounding parenchyma tissue and without being severed, they may bleed profusely and require much more time to stop the bleeding. Consequently, it may be desirable to avoid separation by sharp dissection in situations where large vessels are not first uncovered and exposed.

This technique can also be used on other parenchymal organs such as the pancreas, the kidney, and the lung. In addition, it may also be useful on muscle tissue and subcutaneous fat. It's use can also extend to tumors, cysts or other tissue masses found in the urological or gynecological areas. It would also enable the removal of highly vascularized tumors such as hemangiomas.

The devices disclosed herein are particularly useful as non-coaptive devices that provide cutting of tissue, as well as coagulation, hemostasis and sealing of tissue to inhibit blood and other fluid loss during surgery. In other words, grasping of the tissue is not necessary to shrink, coagulate, cut and seal tissue against blood loss, for example, by shrinking collagen and associated lumens of blood vessels (e.g., arteries, veins) to provided the desired hemostasis of the tissue. Furthermore, the control system of the electrosurgical unit 10 is not necessarily dependent on tissue feedback such as temperature or impedance to operate. Thus, the control system of electrosurgical unit 10 may be open loop with respect to the tissue which simplifies use.

Device 30a disclosed herein may be particularly useful to surgeons to achieve hemostasis after cutting through soft tissue, as part of hip or knee arthroplasty. The distal end portions 148a, 148b can be painted over the raw, oozing surface 202 of tissue 200 to seal the tissue 200 against bleeding, or focused on individual larger bleeding vessels to stop vessel bleeding. As part of the same or different procedure, device 30a is also useful to stop bleeding from the surface of cut bone, or osseous, tissue as part of any orthopaedic procedure that requires bone to be cut. Device 30a may be particularly useful for use during orthopedic knee, hip, shoulder and spine procedures. Additional discussion concerning such procedures may be found in U.S. Publication No. 2006/0149225, published Jul. 6, 2006, and U.S. Publication No. 2005/0090816, published Apr. 28, 2005, which are assigned to the assignee of the present disclosure and are hereby incorporated by reference in there entirety to the extent they are consistent.

As established above, device 30a of the present disclosure inhibit such undesirable effects of tissue desiccation, electrode sticking, char formation and smoke generation, and thus do not suffer from the same drawbacks as prior art dry tip electrosurgical devices. The use of the disclosed devices can result in significantly lower blood loss during surgical procedures. Such a reduction in blood loss can reduce or eliminate the need for blood transfusions, and thus the cost and negative clinical consequences associated with blood transfusions, such as prolonged hospitalization.

While a preferred embodiment of the present disclosure has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes to the extent they are consistent.

Although the present disclosure has been described with reference to preferred embodiments, workers skilled in the art will recognize that changes can be made in form and detail without departing from the spirit and scope of the present disclosure.

What is claimed is:

1. An electrosurgical device to treat tissue in a presence of radio frequency energy and a fluid provided from the device, the device comprising:
    a distal portion comprising a first electrode tip, a second electrode tip and at least one fluid outlet;
    the first electrode tip comprising a first electrode having a distal portion with an electrically conductive spherical surface; the second electrode tip comprising a second electrode having a distal portion with an electrically conductive spherical surface;
    at least one of the first electrode and the second electrode having a blade portion,
    wherein the first electrode and the second electrode are configured to be electrically coupled to a bipolar power output;
    the at least one electrode having the blade portion is configured to be electrically coupled to a monopolar power output; and
    wherein the blade portion extends longitudinally along at least one of the first and the second electrode.

2. The device of claim 1 wherein:
    the blade portion extends from a proximal portion to the distal portion of at least one of the first and the second electrode.

3. The device of claim 1 wherein:
    the blade portion has a cutting edge.

4. The device of claim 3 wherein:
    the cutting edge is an electrosurgical cutting edge.

5. The device of claim 3 wherein:
    the blade portion has opposing sides; the blade portion narrows as the opposing sides approach the cutting edge.

6. The device of claim 5 wherein:
    at least one of the opposing sides comprises a planar surface.

7. The device of claim 5 wherein:
    at least one of the opposing sides comprises a concave surface.

8. The device of claim 5 wherein:
    at least one of the opposing sides comprises a convex surface.

9. The device of claim 1 wherein:
    the at least one fluid outlet further comprises at least one fluid outlet in fluid communication with the first electrode and at least one fluid outlet in fluid communication with the second electrode.

10. The device of claim 9 wherein:
    the at least one fluid outlet in fluid communication with the first electrode is proximal to a distal end of the first electrode; and
    the at least one fluid outlet in fluid communication with the second electrode is proximal to a distal end of the second electrode.

11. The device of claim 9 wherein:
    the at least one fluid outlet in fluid communication with the first electrode is at least partially defined by the first electrode; and
    the at least one fluid outlet in fluid communication with the second electrode is at least partially defined by the second electrode.

12. The device of claim 1 wherein:
    the first electrode is laterally spaced from the second electrode.

13. The device of claim 1 wherein:
    the first electrode is carried by a first tubing segment; and the second electrode is carried by a second tubing segment.

14. The device of claim 13 wherein:
    the first tubing segment is electrically conductive; and the second tubing segment is electrically conductive.

15. The device of claim 14 wherein:
    the electrically conductive first tubing segment is in electrical contact with the first electrode; and
    the electrically conductive second tubing segment is in electrical contact with the second electrode.

16. The device of claim 1 wherein:
    the first electrode is connected at a distal end of a first tubing segment; and
    the second electrode is connected at a distal end of a second tubing segment.

17. The device of claim 16 wherein:
    the first electrode is mechanically joined to the first tubing segment; and
    the second electrode is mechanically joined to the second tubing segment.

18. The device of claim 17 wherein:
    the first electrode is welded to the first tubing segment; and
    the second electrode is welded to the second tubing segment.

19. An electrosurgical device comprising:
    a distal portion comprising a first electrode tip, a second electrode tip and at least one fluid outlet;

the first electrode tip comprising a first electrode having a blade portion extending longitudinally along the first electrode;

the second electrode tip comprising a second electrode having a blade portion extending longitudinally along the second electrode;

each of the first and second electrodes configured to be electrically coupled to a bipolar energy source by first and second bipolar electrical connectors in electrical communication with the first and second electrodes, respectively; and at least one of the first and second electrodes configured to be electrically coupled to a monopolar energy source by a monopolar electrical connector in electrical communication with at least one of the first and second electrodes.

* * * * *